(12) United States Patent
Heinrich et al.

(10) Patent No.: US 8,297,111 B2
(45) Date of Patent: Oct. 30, 2012

(54) ARRANGEMENT FOR DETERMINING A CHARACTERISTIC VARIABLE OF A FLUID, SENSOR DEVICE AND USE IN A MOTOR VEHICLE

(75) Inventors: Stephan Heinrich, Pfeffenhausen (DE); Willibald Reitmeier, Hohenschambach (DE); Denny Schädlich, Neustadt (DE)

(73) Assignee: Continental Automotive GmbH, Hannover (DE)

( * ) Notice: Subject to any disclaimer, the term of this patent is extended or adjusted under 35 U.S.C. 154(b) by 249 days.

(21) Appl. No.: 12/670,532

(22) PCT Filed: Jun. 20, 2008

(86) PCT No.: PCT/EP2008/057872
§ 371 (c)(1),
(2), (4) Date: Jan. 25, 2010

(87) PCT Pub. No.: WO2009/013087
PCT Pub. Date: Jan. 29, 2009

(65) Prior Publication Data
US 2010/0199749 A1    Aug. 12, 2010

(30) Foreign Application Priority Data
Jul. 25, 2007    (DE) .......................... 10 2007 034 585

(51) Int. Cl.
*G01N 11/16*    (2006.01)

(52) U.S. Cl. ...................................... 73/54.26

(58) Field of Classification Search ................. 73/35.05, 73/54.18, 54.19, 54.23–54.27, 64.53
See application file for complete search history.

(56) References Cited

U.S. PATENT DOCUMENTS

| | | | |
|---|---|---|---|
| 2,955,459 A | 10/1960 | Cihelka et al. | |
| 2,973,639 A * | 3/1961 | Banks | 73/54.25 |
| 3,286,507 A * | 11/1966 | Moore | 73/24.05 |
| 3,636,753 A * | 1/1972 | Thiele et al. | 73/54.25 |
| 3,714,814 A * | 2/1973 | Schneiders et al. | 73/54.25 |
| 3,734,119 A * | 5/1973 | Nudds | 137/92 |
| 4,181,029 A | 1/1980 | Talbott, Jr. | |
| 4,488,427 A * | 12/1984 | Matusik et al. | 73/54.23 |
| 4,558,588 A * | 12/1985 | Beaudoin et al. | 73/54.25 |
| 4,601,200 A * | 7/1986 | Stoffelen | 73/290 V |
| 4,704,898 A * | 11/1987 | Thone | 73/54.25 |
| 4,799,378 A * | 1/1989 | Portman et al. | 73/54.27 |
| 4,875,362 A | 10/1989 | Skallen | |
| 4,966,032 A * | 10/1990 | Takeuchi | 73/53.05 |
| 5,377,531 A | 1/1995 | Gomm | |
| 5,394,739 A | 3/1995 | Garvey, III et al. | |
| 5,959,196 A | 9/1999 | Norcross, Jr. | |
| 2009/0064766 A1 | 3/2009 | Scherer | |

FOREIGN PATENT DOCUMENTS

| | | |
|---|---|---|
| CH | 357219 | 11/1961 |
| DE | 575 988 | 1/1933 |
| DE | 36 12 659 A1 | 10/1986 |
| DE | 197 45 807 C2 | 5/1999 |
| DE | 10 2005 012 453 A1 | 9/2006 |

* cited by examiner

*Primary Examiner* — John Fitzgerald
(74) *Attorney, Agent, or Firm* — Cozen O'Connor

(57) ABSTRACT

An arrangement and method for determining a characteristic variable of a fluid having a movably suspended measuring element, a restraining element, an advancing element and a control device. The control device is designed to actuate the restraining element and/or the advancing element in order to move the measuring element between the first measuring point and the second measuring point, to determine a time period which the measuring element requires in order to be moved between the first measuring point and the second measuring point, and to determine a characteristic variable of the fluid on the basis of the determined time period, a predetermined force and a known geometry.

21 Claims, 3 Drawing Sheets

ARRANGEMENT FOR DETERMINING A CHARACTERISTIC VARIABLE OF A FLUID, SENSOR DEVICE AND USE IN A MOTOR VEHICLE

PRIORITY CLAIM

This is a U.S. national stage of application No. PCT/EP2008/057872, filed on Jun. 20, 2008 which claims priority to the German Application No.: 10 2007 034 585.4, Filed: Jul. 25, 2007; the contents of both incorporated herein by reference.

BACKGROUND OF THE INVENTION

1. Field of the Invention

The invention relates to an arrangement for determining a characteristic variable of a fluid. Furthermore, the invention relates to a sensor device for use in such an arrangement and more particularly to the use of such an arrangement in a motor vehicle.

2. Prior Art

The determination of a characteristic variable of a fluid is highly significant in the field of automobiles to sense properties of fuels, lubricants, and other operating media. For example, early detection of a critical decrease in viscosity and therefore in the lubrication capability of an oil can make it possible to determine that it will be necessary to replace the oil to ensure fault-free operation of an internal combustion engine. Furthermore, the viscosity can provide information about aging of oil and the mixing ratio of fuel mixtures, for example gasoline-ethanol or biodiesel mixtures, in particular rapeseed oil methyl ester mixtures. Other characteristic variables, a current flow rate of a fluid in a lubricant circuit or a coolant circuit are also significant.

Methods for determining a viscosity comprise, inter alia, methods for determining a dielectric constant, ultrasonic methods or simple computer-implemented calculation methods which determine the wear of an engine oil on the basis of a use time, engine parameters employed, measured temperatures and similar values.

SUMMARY OF THE INVENTION

In contrast to such indirect methods, the present application describes an arrangement which permits direct determination of a characteristic variable of a fluid. Furthermore, a sensor device for use in such an arrangement is specified.

An object of the invention is achieved by an arrangement for determining a characteristic variable of a fluid, which has the following elements:

a movably suspended measuring element which has a known geometry and can be moved from a first measuring point to a second measuring point within the fluid;

a restraining element by which the measuring element can be secured at the first measuring point, an advancing element by which the measuring element can be actively accelerated in the direction of the second measuring point with a predetermined force, and a control device which is configured to actuate the restraining element and/or the advancing element in order to move the measuring element between the first measuring point and the second measuring point, to determine a time period which the measuring element requires to be moved between the first measuring point and the second measuring point, and to determine a characteristic variable of the fluid based on the determined time period, the predetermined force and the known geometry.

By virtue of the determination of a time period which a movably suspended measuring element requires to move back a predetermined distance through the fluid under a predetermined force of an advancing element, the control device can easily determine a characteristic variable of the fluid.

According to one embodiment of the invention, the restraining element is configured to accelerate the measuring element in the direction of the first measuring point. By virtue of the acceleration of the measuring element in the direction of the first measuring point, the measurement can be repeated as often as desired in that the measuring element is moved back to the starting point, i.e., the first measuring point.

According to a further embodiment of the invention, the restraining element or the advancing element comprises a spring element or an elastic holding element that is suitable for accelerating the measuring element in the direction of the first measuring point or of the second measuring point. The use of a spring element permits a simple, largely constant acceleration in the direction of the spring stress.

According to a further embodiment of the invention, the measuring element comprises a magnetic or paramagnetic material, and the return element and/or the advancing element comprise/comprises a coil for generating an electromagnetic field which is suitable for accelerating the measuring element in the direction of the first measuring point or of the second measuring point. By using a coil to generate an electromagnetic field it is possible to exert a predetermined attraction force or repulsion force in the direction of the first or second measuring element.

According to a further embodiment of the invention, the arrangement has a first or a second sensor configured to output a first or a second signal if the measuring element is located at the first or the second measuring point. By using a first or second sensor, the time when the first or second measuring point is exited or reached can easily be determined.

According to a further embodiment of the invention, the arrangement comprises a first or a second sensor, wherein the first and the second sensors are embodied as switching contacts which close or open a circuit when the first measuring point is exited or the second measuring point is reached.

As a result of the opening or closing of a circuit when the first measuring point is exited or the second measuring point is reached, the control device can easily determine the time period which the measuring element requires in order to move from the first measuring point to the second measuring point.

According to a further embodiment of the invention, the predetermined force and the geometry of the measuring element are dimensioned such that the measuring element can be moved from the first measuring point to the second measuring point at a speed at which a laminar flow is formed in the fluid. When a laminar flow is formed in the fluid, particularly simple and precise measurement and calculation of the characteristic variable is possible.

According to a further embodiment of the invention, the movement of the measuring element from the first measuring point to the second measuring point extends a substantially horizontal plane. By virtue of the fact that the measuring element moves in a substantially horizontal plane, that is to say perpendicularly with respect to the force of gravity, the described arrangement becomes independent of the force of gravity acting on it.

According to a further embodiment of the invention, the measuring element is suspended from a rocking arm which can move in one spatial direction. Suspension from a rocking arm makes it possible to ensure that the measuring element is guided along a measured section.

According to a further embodiment of the invention, the measuring element is of flexible design and is clamped at a fixing point. Using a flexible measuring element makes it possible to dispense with the use of a mechanical bearing.

According to a further embodiment of the invention, the arrangement comprises a sensor element for determining a bending of the flexible measuring element. Determining the bending makes it possible to infer the position of the measuring element.

According to a further embodiment of the invention, the control device is configured to actuate the restraining element and/or the advancing element to move the measuring element out of a rest position into a deflected position and back into the rest position. Deflecting the measuring element out of a rest position makes it possible to carry out a simple, repeatable measurement.

According to a further embodiment of the invention, the first measuring point and/or the second measuring point correspond/corresponds spatially to the position of rest. The double use of the position of rest as a measuring point makes it possible to dispense with the use of additional measuring points.

According to a further embodiment of the invention, the arrangement comprises a temperature sensor for determining a temperature of the fluid. Determining the temperature of the fluid makes it possible to carry out temperature equalization during the determination of the characteristic variable.

According to a further embodiment of the invention, the arrangement comprises an acceleration sensor for determining an acceleration of the arrangement in a horizontal plane. Determining the acceleration of the arrangement makes it possible to carry out equalization for external acceleration forces which occur during the measurement.

According to a further embodiment of the invention, the determined characteristic variable of the fluid comprises at least one of the following parameters: a viscosity, a flow rate, a degree of soiling, a degree of aging, a lubrication capability or a mixing ratio. Determining one or more of the abovementioned parameters makes it possible to characterize a fluid better.

The described arrangement is suitable in particular for use in a motor vehicle, for example a road vehicle or rail vehicle, an aircraft or a ship.

BRIEF DESCRIPTION OF DRAWINGS

The invention will be explained in more detail below using exemplary embodiments and with reference to drawings in which.

DETAILED DESCRIPTION OF THE PREFERRED EMBODIMENTS

Firstly, an explanation will be given of the determination of a characteristic variable of a fluid, here the viscosity thereof, by a known arrangement. For this purpose, FIG. 6 is a schematic design of a ball-type or falling-body-type viscometer in which a falling body 1, generally a ball with a known radius r, drops to the ground through a liquid column 2 whose viscosity is to be determined.

Figure 6:
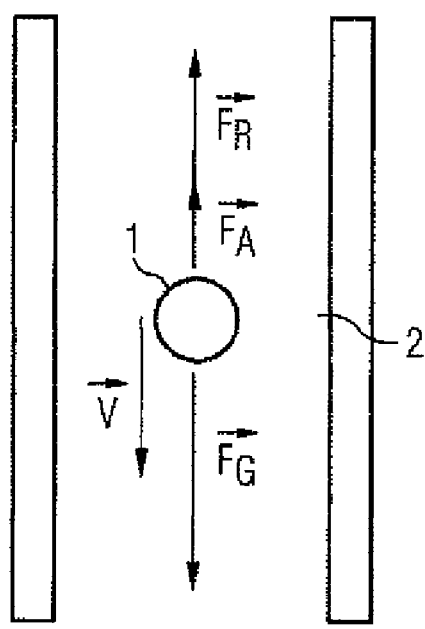
FIG. 6 is a schematic illustration of a ball-type viscometer according to the prior art.

Essentially three forces, indicated by arrows in FIG. 6, act on the falling body 1. Due to gravity, the falling body 1 is accelerated in the downward direction. This force is denoted by the reference $F_G$ in FIG. 6. The buoyancy force $F_A$ and the frictional force $F_R$ act on the falling body 1 in the opposite direction, that is to say in the upward direction. The buoyancy force $F_A$ is determined by the volume and the density of the falling body 1 and the density of the liquid and is therefore constant. The frictional force $F_R$ depends on the speed v with which the falling body 1 moves through the liquid column 2 and it generally increases as the speed v rises.

Taking a position of rest or an initial speed $v_0$ as the starting point, the falling body 1 is initially accelerated by the gravitational force $F_G$ until an equilibrium of forces occurs between the gravitational force $F_G$ and the buoyancy force $F_A$ and the frictional force $F_R$ The falling body 1 therefore drops at a constant speed v after this equilibrium is established, and in this context the dynamic viscosity η of the liquid column 2 can be determined indirectly on the basis of Stokes' friction law.

A disadvantage of the described falling-body-type viscometer is its relatively complex design, which cannot be used for fully automatic measurement in a closed oil circuit, for example that of an internal combustion engine. Furthermore, it is generally not possible to determine the viscosity until after the equilibrium condition has been established. In addition, the effects of impacts due to unevennesses in the road, are superimposed on the gravitational force $F_G$ acting on the falling body and therefore falsify the measurement result.

Figure 1:
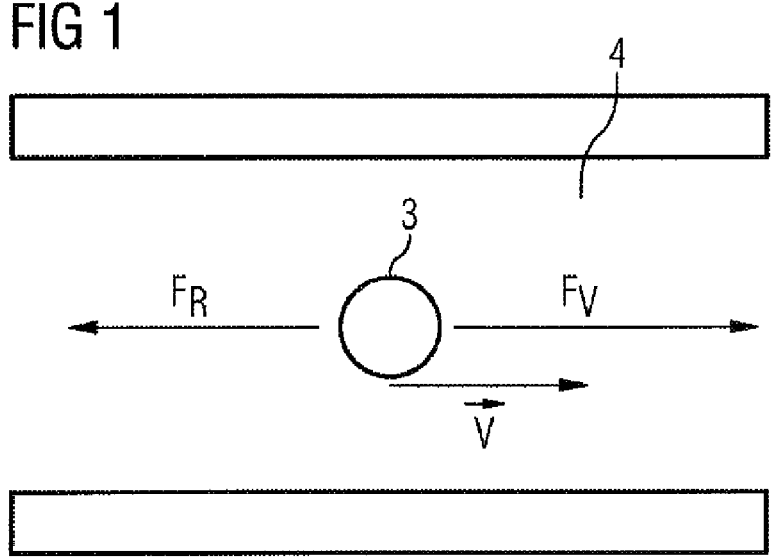
FIG. 1 is a schematic illustration of the forces acting in a horizontal arrangement.

FIG. 1 shows a horizontal arrangement for determining a characteristic variable, in particular a viscosity, according to one embodiment of the invention. According to the arrangement in FIG. 1, a measuring element 3 is movably arranged in a fluid 4. The measuring element 3 is a ball or another body with a known geometry. The fluid may be a fuel such as gasoline or diesel fuel, a mixture of various types of fuel such as for example the fuel mixture E50 with 50% ethanol and 50% gasoline, or biodiesel, that is to say a rapeseed oil methyl ester mixture (RME). Other liquids such as, engine oils with different viscosities and brake fluids can also serve as the fluid 4. Characteristic variables of gases can also be determined, and in this case a particularly large measuring element 3 or one small acceleration force should be used owing to the very much lower density of the fluid.

The movement of the measuring element 3 is limited to a substantially horizontal plane in the arrangement illustrated in FIG. 1. In this way, the gravitational force $F_G$ is prevented from influencing the movement of the measuring element 3. Only the frictional force $F_R$ and an opposed advancing force $F_V$ therefore act on the measuring element 3, as is illustrated in FIG. 1. The advancing force $F_V$ may be, for example, the force of a tensioned spring or that of a solenoid that acts on the measuring element 3. Owing to the acceleration due to the advancing force $F_V$, the measuring element 3 is accelerated to the right in FIG. 1.

In this context, the speed v of the measuring element 3 increases with time.

If a laminar flow is formed as a result of the movement of the ball, that is to say that no eddying occurs in the fluid with the dynamic viscosity η, the frictional force $F_R$ is determined by Stokes' law, in which context the following applies to a ball with the radius r and the speed v:

$$F_R = 6 \cdot \pi \cdot \eta \cdot r \cdot v$$

When a spring is used to accelerate the measuring element 3, the following applies to the advancing force $F_V$:

$$F_V = D \cdot \Delta l$$

where $\Delta l$ represents the deflection of the measuring element 3 or the extension of the spring, and D represents the spring constant.

As a result, in the equilibrium of forces ($F_V = F_R$) the following applies:

$$D \cdot \Delta l = 6 \cdot \pi \cdot \eta \cdot r \cdot v \rightarrow \eta = \frac{D \cdot \Delta l}{6 \cdot \pi \cdot r \cdot v}$$

When the speed is increasing, the following applies for the distance traveled in the special case $v_0=0$, that is to say out of the position of rest of the measuring body 3:

$$\Delta l = \frac{1}{2} \cdot v \cdot t \rightarrow v = \frac{2 \cdot \Delta l}{t}$$

The following applies to a constant speed v, that is to say in the case of equilibrium:

$$v = \frac{\Delta l}{t}$$

When inserted into the viscosity equation this yields:

$$\eta = \frac{D \cdot t}{12 \cdot \pi \cdot r}$$

and, respectively, $$\eta = \frac{D \cdot t}{6 \cdot \pi \cdot r}$$

In practice, one or other case or a combination of the two cases occurs, depending on the viscosity of the fluid and the arrangement of the sensor. The proportionality constant should preferably be determined for the intended measuring range and used for calibrating the sensor arrangement.

As a result, the following dependence occurs in the laminar case:

$$\eta \sim t$$

In the turbulent case when eddying is formed in the fluid 4, Newtonian friction must be used instead of Stokes' friction:

$$F_R = \frac{1}{2} \cdot \rho \cdot A \cdot v^2 \cdot c_w$$

Here, $\rho$ stands for the mass density of the fluid. The coefficient $c_w$ of flow resistance is between 0.055 for a streamlined shape and 1.3 when the geometry is particularly unfavorable. A ball as a measuring element 3 has a coefficient $c_w$ of flow resistance of 1.0.

The following applies to the projected surface A of a ball with a radius r:

$$A = r^2 \cdot \pi$$

This yields the following in the equilibrium of forces ($F_V = F_R$):

$$D \cdot \Delta l = \frac{1}{2} \cdot \rho \cdot r^2 \cdot \pi \cdot v^2 \cdot c_w \rightarrow \rho = \frac{2 \cdot D \cdot \Delta l}{r^2 \cdot \pi \cdot v^2 \cdot c_w}$$

The following applies to the kinematic viscosity $u_{kin}$:

$$u_{kin} = \frac{\eta}{\rho} \rightarrow \eta = \rho \cdot u_{kin}$$

where $\eta$ represents the dynamic viscosity or simply the viscosity. Using the above viscosity equation the following is obtained:

$$\eta = \frac{2 \cdot D \cdot \Delta l \cdot u_{kin}}{r^2 \cdot \pi \cdot v^2 \cdot c_w}$$

where $$v = \frac{2 \cdot \Delta l}{t}$$

$$\eta = \frac{2 \cdot D \cdot \Delta l \cdot t^2 \cdot u_{kin}}{4 \cdot \Delta l^2 \cdot r^2 \cdot \pi \cdot c_w} = \frac{D \cdot t^2 \cdot u_{kin}}{2 \cdot \Delta l \cdot r^2 \cdot \pi \cdot c_w}$$

In the turbulent case, this therefore results in the following dependence:

$$\eta \sim t^2 \cdot u_{kin}$$

To differentiate between the laminar case and the turbulent case, it is possible, for example, to determine the Reynolds number Re of a given arrangement, with a turbulent flow forming above a limiting value $Re_{crit}$ and a laminar flow forming below this limiting value $Re_{crit}$. For a ball-shaped measuring element 3 $Re_{crit}=2$. Owing to the simpler relationships, in particular the laminar case is suitable in the field of motor vehicle engineering.

The abovementioned formulas are dependent on the geometric conditions of the measuring element 3. When a non-ball-shaped measuring element 3 is used, the conditions which are used as a basis must be correspondingly adapted. Instead of an analytical determination of the relationships, it is also possible to use a calibration method for determining reference values, in particular in the case of measuring elements with irregular shapes.

Figure 2:
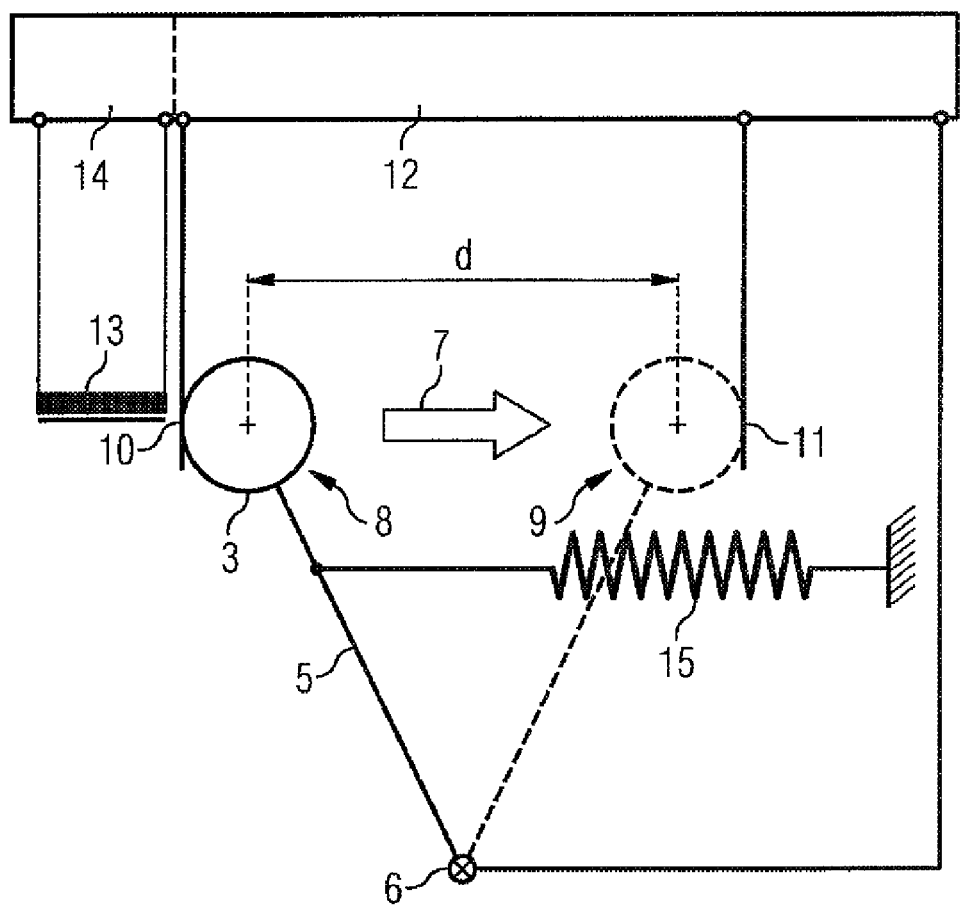
FIG. 2 is an arrangement for determining a characteristic variable of a fluid according to one embodiment of the invention.

FIG. 2 is a schematic illustration of a plan view of an arrangement according to an embodiment of the invention.

A measuring element 3 is suspended by a rocking arm 5 from an axis 6 or is engaged in a bearing in such a way that it can move essentially only on an arc within a plane. Acceleration in the direction of arrow 7 is brought about through the action of an advancing force $F_V$. In this context, the advancing force $F_V$ can be exerted, by a spring or by an energized coil which attracts a magnetic or paramagnetic component of the measuring element 3 or of the rocking arm 5. In the illustrated exemplary embodiment, the measuring element 3 is moved by the spring element 15 from a first measuring point 8 to a second measuring point 9, which measuring points 8, 9 are arranged at a predetermined distance d from one another.

At the first measuring point 8, the measuring element 3 closes a first contact 10, which is opened when the measuring element 3 leaves first measuring point 8. The second measuring point 9 forms a second contact 11 which is closed when the measuring element 3 reaches the second measuring point 9. At the first contact 10 and the second contact 11, a timing device 12 is connected that determines a time between the opening of the first contact 10 and the closing of the second contact 11. Based on the determination of this time period, inter alia the dynamic viscosity η of the fluid 4 can be determined in accordance with the above derivation.

Furthermore, the arrangement according to FIG. 2 comprises a restraining element, in the exemplary embodiment a coil 13. The coil 13 is connected to a control device 14, which is connected to the timing device 12 or includes the latter. The control device 14 can switch off at any time the coil 13 which holds the measuring element 3 at the first measuring point. After the coil 13 has been switched off, the measuring element 3 is accelerated in the direction of the arrow 7 by the advancing force $F_V$ in the direction of the second measuring point 2. At the same time, the first contact 10 is broken.

Instead of a signal of the first contact 10, the control device 14 can also transmit a signal to the timing device 12 to characterize the start of a measurement. The first contact 10 can be dispensed with in such an embodiment. If, instead of the spring element 15, a second coil is used to accelerate the measuring element 3 from a position of rest, the starting time of the measurement can also be determined by the time of energization of the second coil.

Instead of contacts it is possible to use light barriers or other sensors to detect the position of the measuring element 3. It is irrelevant here whether a circuit is opened or closed by means of the sensor or the sensors are changed in some other way in order to signal the position of the measuring element 3.

In the exemplary embodiment illustrated in FIG. 2, the coil 13 is also used to return the measuring element 3 to the first measuring point 8 after the measurement has taken place. For this purpose, the force exerted by the coil 13 must exceed the spring force of the spring element 15.

Alternatively, an embodiment with two coils 13, in which the electromagnetic attraction force is used to accelerate the measuring element 3 both in the advancing direction and in the return direction, is also possible. If the arrangement including the coils 13 has a symmetrical configuration, a measurement can be carried out both in the first and in the second directions, with the function of the advancing element and restraining element and of the first and second measuring points being respectively interchanged between two successive measurements.

Figure 3:
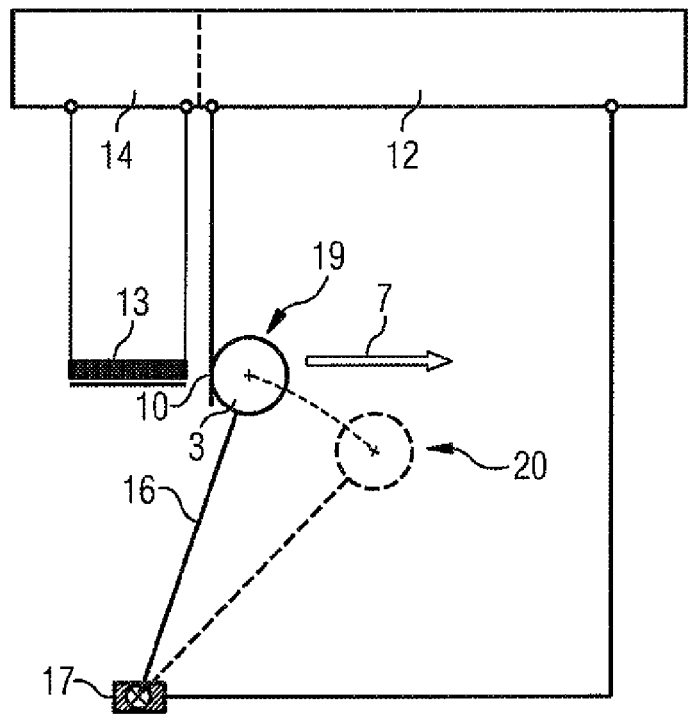
FIG. 3 is an arrangement for determining a characteristic variable of a fluid according to a further embodiment.

In particular the use of a relay which is, if appropriate, modified and whose switching contacts dip at least partially into the fluid 4 to be measured is suitable for the technical implementation of the arrangement according to FIG. 2 or 3.

In this context, a relay makes available, in particular, first and second contacts 10 and 11 for the time measurement. Furthermore, the contact arm of a relay can be used as a rocking arm 5. Spring elements 15 and coils 13 of a relay serve as advancing elements and, respectively, as a restraining element, or vice versa. A relay therefore only has to measures around a suitable control device which, on the one hand, actuates the coils 13 of the relay in a suitable way in order to carry out the measurement, and which, on the other hand, measures the time which the measuring element 3 requires to travel from the first measuring point 8 to the second measuring point 9.

In a further embodiment, the control device 14 is configured to determine a characteristic variable of the fluid 4, in particular the dynamic viscosity η thereof, on the basis of the measured time period, the known geometry of the measuring element 3 and the distance d. For example a microprocessor installed in the control device 14 is capable, of determining the currently measured dynamic viscosity η based on known calibration points. Alternatively, this determination can be performed by another component, for example an on-board computer of a motor vehicle.

In order to counteract wear, in particular, of the electrical contacts, that is to say the first contact 10 and the second contact 11, it is also possible to clean the arrangement automatically at regular time intervals. For example, it is possible to "burn clean" the contacts 10 or 11 by applying an alternating voltage between individual measurements. At the same time, particles of dirt or other impurities are removed from the spring element 15 or the measuring element 3. Such burning clean is suitable in particular when the arrangement is used in conjunction with particularly heavy oils or other liquids with a comparatively high degree of admixture of extraneous substances.

FIG. 3 is a second embodiment of an arrangement for determining a characteristic variable of a fluid 4. The arrangement according to FIG. 3 comprises a measuring element 3 which, in a position of rest 19, is connected to an electrical first contact 10. A coil 13 repels the measuring element 3, which comprises, a permanent magnet, in the direction of the arrow 7, with the result that said measuring element 3 exits the position of rest 19. The coil 13 is actuated by means of a control device 14 which is connected to a timing device 12.

In contrast to the embodiment according to FIG. 2, the measuring element 3 is clamped tightly at a fixing point 17 by an elastic holding element 16, with the holding element 16 being pre-stressed with respect to the first contact 10. The elastic holding element 16 therefore exerts a force on the measuring element 3 which drives the measuring element 3 back in the direction of the position of rest 19.

To determine the characteristic variable of the fluid 4, the measuring element 3 of the arrangement according to FIG. 3 is firstly pushed away from the position of rest 19 by the coil 13, with the result that the measuring element 3 assumes a deflected position 20 which is illustrated by dashed lines in the FIG. 3. After a predetermined time, the coil 13 is switched off by the control device 14, with the result that the measuring element 3 returns to its original position of rest 19 at the first measuring point and closes the first contact.

According to a first embodiment, the coil 13 is only activated for a very short time period, with the result that the acceleration of the measuring element 3 from the position of rest 19 is an impulse, and the time period which is determined by the timing device 12 comprises the time for the measuring element 3 to travel from the position of rest 19 into the deflected position 20 and back to the position of rest 19. Here, the time period of the individual travel corresponds to half the measured overall time. In this exemplary embodiment, the position of rest 19 serves both as a first measuring point and as a second measuring point.

According to one alternative embodiment, the coil 13 remains activated until the measuring element 3 is reliably in a state of equilibrium in the deflected position 20, in which state the repulsion force of the coil 13 and the restoring force of the elastic holding element 16 cancel one another out. The timing device 12 begins to measure the time by deactivating the coil 13 and therefore measures the time period which the measuring element 3 requires out of the deflected position 20 back to the position of rest 19. Here, the deflected position 20 therefore serves as a first measuring point, while the position of rest 19 serves as a second measuring point.

Figure 4:
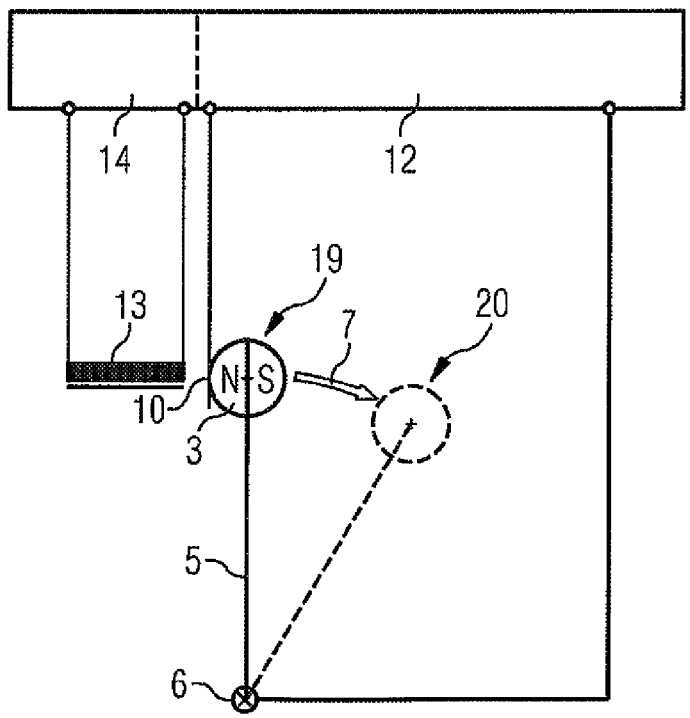
FIG. 4 is an arrangement for determining a characteristic variable of a fluid according to a further embodiment.

FIG. 4 shows a further embodiment of the invention. The arrangement according to FIG. 4 comprises, a timing device 12 with a control device 14 to which a coil 13 is connected.

The timing device 12 is connected to a first contact 10 which is closed if a measuring element 3 is in a position of rest 19. The measuring element 3 is attached to a rocking arm 5 which is movably mounted at an axis 6.

In the exemplary embodiment according to FIG. 4, the measuring element 3 is a magnetic measuring element with a north pole N and a south pole S. The measuring element 3 can therefore be both repelled and attracted by the coil 13. In order to change the direction of the force between the coil 13 and the measuring element 3, all that is necessary is to reverse the polarity of the current through the coil 13 by the control device 14.

To determine the characteristic variable of the fluid 4, the measuring element 3 is initially repelled by the coil 13, with the result that it moves into a deflected position 20 in the direction of the arrow 7. After an equilibrium has been established, the polarity of the coil 13 is reversed and the measurement of time by the timing device 12 starts. Starting from this time, the coil 13 attracts the measuring element 3 in the direction of the position of rest 20. Based on the time period which the measuring element 3 requires from the deflected position 20 back to the position of rest 19, it is possible, for example, to determine the dynamic viscosity $\eta$ of the fluid 4 as described above.

Figure 5:
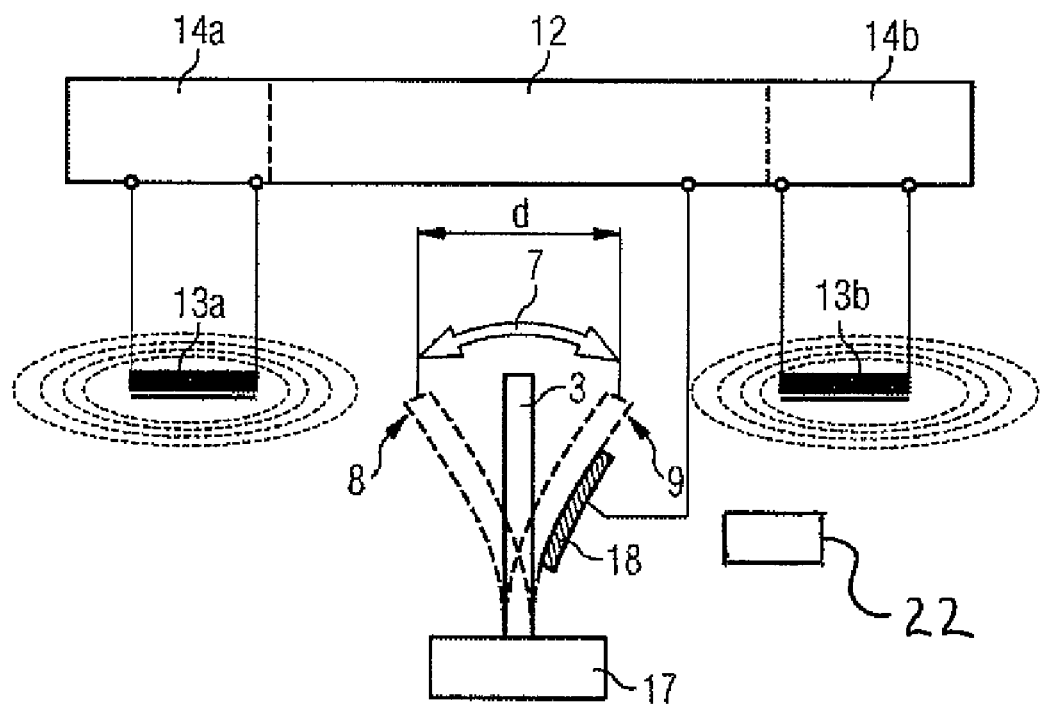
FIG. 5 is an arrangement for determining a characteristic variable of a fluid according to a further embodiment.

FIG. 5 shows a further embodiment of an arrangement for determining a characteristic variable of a fluid 4. According to FIG. 5, a timing device 12 is connected to two control devices 14a and 14b. The control devices 14a and 14b are each connected to one coil 13a or 13b, respectively. Between the two coils 13a and 13b a measuring element 3, in the exemplary embodiment a flexible metal strip, is clamped in at a fixing point 17.

Furthermore, a sensor element 18, which is connected to the timing device 12 and senses bending of the measuring element 3, is arranged on the measuring element 3. The sensor element 18 may comprise, for example, a thin piezo-electric material whose voltage depends on the degree of bending of the metal strip. Alternatively, a strain gauge whose electrical resistance depends on the bending of the measuring element 3 can also be used.

By alternately switching on the coils 13a and 13b by the control devices 14a and 14b, respectively, the measuring element 3 is made to oscillate mechanically between a first measuring point 8 and a second measuring point 9 from sensor data received by the sensor element 18, the timing device 12 can determine at which location the measuring element 3 is located at any time. Based on this information, the timing device 12 can also determine the distance d and the period length of the oscillation of the measuring element 3. Based on the distance d and the time period of the movement of the measuring element 3 from the first measuring point 8 to the second measuring point 9, it is possible, for example, to determine the dynamic viscosity $\eta$ of the fluid 4 as described above.

If the dynamic viscosity $\eta$ of the fluid 4 is known, the flow rate within a line through which the fluid 4 is flowing can also be determined with one of the arrangements described above. For example, it is possible to determine lengthening and shortening of the time which the measuring element 3 requires, compared to a reference value obtained in a fluid 4 at rest, for its movement in order to travel from the first measuring point 8 to the second measuring point 9.

Under certain circumstances, it is advantageous to carry out temperature compensation both during the measurement of viscosity and during the determination of the flow rate. Particularly in the case of lubricants, the viscosity is highly temperature-dependent. In order to determine operating parameters such as, for example, the degree of soiling or the degree of aging of an oil independently of temperature, the measured dynamic viscosity $\eta$ of the fluid 4 should therefore be standardized by means of a predetermined characteristic curve.

According to a further embodiment, the arrangement therefore has a temperature sensor 22 which determines the temperature of the fluid 4 in the region of the measuring element 3. According to one embodiment, the temperature sensor is connected to the control device 14. Alternatively, temperature compensation can also be carried out without using an additional temperature sensor in the arrangement. For example, sensor data which are acquired at a different location in an oil circuit can, for this purpose, be made available via a communication device of a motor vehicle, for example what is referred to as a CAN bus. The correction can then be carried out by means of the control device 14 or a microcontroller, for example an on-board computer, which is different therefrom.

A horizontal arrangement for determining a characteristic variable of a fluid 4 has the particular feature of being resistant to unevennesses in the road. Nevertheless, acceleration forces act on the arrangement when there are strong lateral accelerations or longitudinal accelerations. In one preferred embodiment, these additionally occurring forces are compensated by acquiring and taking into account reference values. For example, the arrangement can be equipped for this purpose with additional acceleration sensors which determine acceleration in the direction of movement of the rocking arm 5. Alternatively or additionally, a plurality of measured values can also be integrated over a time period in order to determine a statistical mean value of the characteristic variable. In this case, or when there are comparatively low lateral accelerations, it is possible to dispense with compensation.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An arrangement for determining a characteristic variable of a fluid, comprising:
    a movably suspended measuring element having a known geometry, the movably suspended measuring element configured to move in a substantially horizontal plane from a first measuring point to a second measuring point within the fluid;
    a restraining element configured to secure the measuring element at the first measuring point;
    an advancing element configured to accelerate the measuring element towards the second measuring point with a predetermined force; and a control device configured to:
  actuate at least one of the restraining element and the advancing element to move the measuring element between the first measuring point and the second measuring point;
  determine a time period for the measuring element to move between the first measuring point and the second measuring point; and
  determine a characteristic variable of the fluid based at least in part at least one of the determined time period, the predetermined force, and the known geometry.

2. The arrangement as claimed in claim 1, wherein the fluid comprises at least one of:
  a lubricant,
  engine oil,
  gear oil,
  fuel,
  gasoline,
  diesel,
  ethanol,
  rapeseed oil methyl ester,
  transmission fluid,
  brake fluid, and
  hydraulic oil.

3. The arrangement as claimed in claim 1, wherein the restraining element is configured to accelerate the measuring element towards the first measuring point.

4. The arrangement as claimed in claim 1, wherein at least one of the restraining element and the advancing element comprises at least one of:
  a spring element; and
  an elastic holding element,
  the spring element and the elastic holding element configured to accelerate the measuring element towards at least one of the first measuring point and the second measuring point.

5. The arrangement as claimed in claim 1, wherein the measuring element comprises a magnetic or paramagnetic material, and at least one of the return element and the advancing element comprises a coil configured to generate an electromagnetic field to accelerate the measuring element towards at least one of the first measuring point and the second measuring point.

6. The arrangement as claimed in claim 1, wherein the predetermined force and the geometry of the measuring element are configured such that the measuring element is adapted to move from the first measuring point to the second measuring point at a speed at which a laminar flow is formed in the fluid.

7. The arrangement as claimed in claim 1, wherein the measuring element is suspended from a rocking arm configured to move in one spatial direction.

8. The arrangement as claimed in claim 1, further comprising a temperature sensor configured to determine a temperature of the fluid.

9. The arrangement as claimed in claim 1, further comprising an acceleration sensor configured to determine an acceleration of the arrangement in a horizontal plane.

10. The arrangement as claimed in claim 1, wherein the determined characteristic variable of the fluid comprises at least one of:
  a viscosity,
  a flow rate,
  a degree of soiling,
  a degree of aging,
  a lubrication capability, and
  a mixing ratio.

11. The arrangement as claimed in claim 1, further comprising a first sensor configured to output a first signal if the measuring element is located at the first measuring point.

12. The arrangement as claimed in claim 11, further comprising a second sensor configured to output a second signal if the measuring element is located at the second measuring point.

13. The arrangement as claimed in claim 12, wherein at least one of the first and second sensors is configured as a switching contact.

14. The arrangement as claimed in claim 13, wherein the first and second sensors are embodied as switching contacts of a relay arranged at least partially in the fluid.

15. The arrangement as claimed in claim 1, wherein the measuring element is of flexible design and is clamped at a fixing point.

16. The arrangement as claimed in claim 15, wherein the arrangement comprises a sensor element for determining a bending of the flexible measuring element.

17. The arrangement as claimed in claim 1, wherein the control device is further configured to actuate at least one of the restraining element and the advancing element to move the measuring element out of a rest position into a deflected position and back into the rest position.

18. The arrangement as claimed in claim 17, wherein one of the first measuring point and the second measuring point corresponds to the rest position.

19. A sensor device comprising:
  a movably suspended measuring element having a known geometry configured to be movable from a first measuring point to a second measuring point;
  a restraining element configured to secure the measuring element at the first measuring point;
  an advancing element configured to accelerate the measuring element towards the second measuring point with a predetermined force; and
  at least one sensor configured to output a signal when the measuring element is located at one of the first measuring point and the second measuring point.

20. A method for determining a characteristic variable of a fluid, comprising:
  providing a measuring element having a known geometry, the measuring element configured to move in a substantially horizontal plane from a first measuring point to a second measuring point within the fluid;
  securing the measuring element with a restraining element at the first measuring point;
  accelerating the measuring element from the first measuring point to the second measuring point with a predetermined force; and
  determining a time period for the measuring element to move between the first measuring point and the second measuring point; and
  determining a characteristic variable of the fluid based at least in part on at least one of the determined time period, the predetermined force, and the known geometry.

21. The method of claim 20, wherein the fluid is an operating medium of a motor vehicle, and the method comprises determining a state of the operating medium has on the characteristic variable.

* * * * *